(12) United States Patent
Sageder et al.

(10) Patent No.: US 10,987,044 B2
(45) Date of Patent: Apr. 27, 2021

(54) UROFLOWMETRY SYSTEMS, DEVICES AND METHODS

(71) Applicant: MINZE NV, Antwerp (BE)

(72) Inventors: Josef Sageder, Pfarrkirchen (AT); Jiri Vermeulen, De Klinge (BE)

(73) Assignee: MINZE NV, Antwerp (BE)

( * ) Notice: Subject to any disclaimer, the term of this patent is extended or adjusted under 35 U.S.C. 154(b) by 297 days.

(21) Appl. No.: 15/748,763

(22) PCT Filed: Aug. 26, 2016

(86) PCT No.: PCT/EP2016/070180
§ 371 (c)(1),
(2) Date: Jan. 30, 2018

(87) PCT Pub. No.: WO2017/036952
PCT Pub. Date: Mar. 9, 2017

(65) Prior Publication Data
US 2019/0008439 A1    Jan. 10, 2019

(30) Foreign Application Priority Data

Aug. 28, 2015 (EP) .................................... 15182885

(51) Int. Cl.
*A61B 5/20* (2006.01)
*A61B 10/00* (2006.01)
(Continued)

(52) U.S. Cl.
CPC ............ *A61B 5/208* (2013.01); *A61B 5/0004* (2013.01); *A61B 5/6891* (2013.01); *A61B 5/721* (2013.01);
(Continued)

(58) Field of Classification Search
None
See application file for complete search history.

(56) References Cited

U.S. PATENT DOCUMENTS

2007/0179389 A1* 8/2007 Wariar ............... A61B 5/14507
600/508
2010/0064797 A1    3/2010 Hirao
(Continued)

FOREIGN PATENT DOCUMENTS

| EP | 2 246 675 A1 | 11/2010 |
| JP | 2002 186601 A | 7/2002 |
| WO | 2013021207 A1 | 2/2013 |

OTHER PUBLICATIONS

PCT International Search Report and Written Opinion dated Nov. 16, 2016 for PCT International Patent Application No. PCT/EP2016/070180, 13 pages.

*Primary Examiner* — Etsub D Berhanu
*Assistant Examiner* — Aurelie H Tu
(74) *Attorney, Agent, or Firm* — Amster, Rothstein & Ebenstein LLP

(57) ABSTRACT

The present invention includes devices, systems and methods in the field of uroflowmetry, more specifically in the field of home uroflowmetry. In one aspect, the present invention discloses a core unit comprising an accelerometer; a urine detector; a weight sensor; a communication module; a microprocessor; and, an energy source. Further provided is a uroflowmetry device comprising said core unit.

7 Claims, 12 Drawing Sheets

(51) Int. Cl.
  *A61B 5/00* (2006.01)
  *G01N 33/493* (2006.01)
  *G01N 27/22* (2006.01)

(52) U.S. Cl.
  CPC .............. *A61B 5/742* (2013.01); *A61B 10/007* (2013.01); *G01N 33/493* (2013.01); *A61B 2560/0209* (2013.01); *A61B 2560/0214* (2013.01); *A61B 2562/0219* (2013.01); *A61B 2562/0257* (2013.01); *A61B 2562/18* (2013.01); *G01N 27/22* (2013.01)

(56) References Cited

U.S. PATENT DOCUMENTS

| | | |
|---|---|---|
| 2010/0179912 A1 | 7/2010 | Curotto |
| 2010/0206642 A1 | 8/2010 | Currotto |
| 2011/0119028 A1 | 5/2011 | Bishop |
| 2012/0226196 A1 | 9/2012 | Dimino et al. |
| 2014/0094665 A1* | 4/2014 | Ron .................... A61B 5/20 600/309 |
| 2014/0182951 A1 | 7/2014 | Currotto |
| 2014/0296746 A1 | 10/2014 | Whitaker |
| 2015/0020298 A1* | 1/2015 | Hsu .................... E03D 5/105 4/305 |
| 2015/0057111 A1* | 2/2015 | Tremblay-Munger ................. A63B 60/00 473/446 |
| 2015/0112230 A1* | 4/2015 | Iglesias .............. A61B 5/6898 600/593 |
| 2015/0342574 A1* | 12/2015 | Hall .................... A61B 10/007 600/573 |
| 2016/0187188 A1 | 6/2016 | Curotto |
| 2016/0310711 A1* | 10/2016 | Luxon .................. A61M 27/00 |
| 2017/0020433 A1* | 1/2017 | Hotaling ............... A61B 5/208 |
| 2017/0296101 A1* | 10/2017 | Alberts ............... G16H 50/30 |

\* cited by examiner

SECTION A-A

UROFLOWMETRY SYSTEMS, DEVICES AND METHODS

FIELD OF THE INVENTION

The present invention includes devices, systems and methods in the field of uroflowmetry, more specifically in the field of home uroflowmetry. In one aspect, the present invention discloses a core unit comprising an accelerometer; a urine detector; a weight sensor; a communication module; a microprocessor; and, an energy source. Further provided is a uroflowmetry device comprising said core unit.

BACKGROUND

Uroflowmetry is a simple, non-invasive diagnostic procedure in which the flow rate of urine is measured over time. The information obtained in uroflowmetry tests helps evaluating the function of the lower urinary tract and/or it may help determining whether normal urine flow is obstructed.

Being simple and non-invasive, uroflowmetry is generally included in the initial work-up of incontinent subjects. In particular, uroflowmetry is generally performed as a diagnostic prior to any urethral instrumentation.

Many different factors determine the reliability of uroflowmetry tests. A first factor is the "fullness" of the bladder prior to urination. Ideally, patients should void with a "comfortably full bladder". Since filling of the bladder is an involuntary process which can only be influenced indirectly through the consumption of foods and beverages, letting patients void with a comfortably full bladder can be challenging indeed when operating in a clinical setting.

In addition, uroflowmetry measurements may be influenced by a variety of factors, including body movement and disturbance of urine receptacles during urination. When a uroflowmetry measurement is disturbed, and when it is interpreted not taking the disturbance into account, faulty diagnosis may result. As decisions to undertake invasive procedures are often based on the results of uroflowmetry tests, such faulty diagnosis may be costly, both in terms of human discomfort and in terms of capital expenditures.

Ideally, multiple uroflowmetry measurements are performed. However, given the time it takes for a person's bladder to fill, performing these tests in a hospital setting may be impractical.

In fact, the most practical setting for performing uroflowmetry tests would be in the privacy and comfort of a patient's home. However, due to limited oversight by a physician, interpreting the validity of home uroflowmetry tests may be more challenging compared to interpreting the validity of uroflowmetry tests taken in a clinical setting. Also, patient compliance with taking uroflowmetry tests may be less at home compared to in a clinical setting.

Accordingly, there is a need for uroflowmetry systems which allow reliably performing uroflowmetry at home while facilitating satisfactory patient compliance.

SUMMARY OF THE INVENTION

In a first aspect, the present invention relates to a core unit of a uroflowmetry device, the core unit comprising at least
  an accelerometer:
  a urine detector;
  a weight sensor;
  a communication module;
  a microprocessor; and,
  an energy source.

Preferably, the core unit as described herein further comprises a proximity sensor. Preferably, the core unit as described herein further comprises an inductive power module. Preferably, the core unit as described herein further comprises a memory module.

Preferably, the core unit as described herein provides that the accelerometer is configured for:
  detecting an acceleration in a lateral direction;
  detecting shocks; and/or
  detecting the orientation of the core unit with respect to the horizontal plane.

Preferably, the core unit as described herein further comprises a waterproof housing, in which at least the accelerometer, the urine detector, the weight sensor, the communication module, the energy source, and optionally the proximity sensor, are embedded.

Preferably, the core unit as described herein provides that the urine detector comprises a capacitive sensor.

Preferably, the core unit as described herein provides that the weight sensor is configured for detecting the weight of urine and/or the change of the weight of urine in time.

In an additional aspect the present invention also relates to a receptacle configured for operationally coupling with the core unit as described herein, wherein said receptacle comprising urine analysis sensors for providing a chemical analysis of urine.

In an additional aspect the present invention also relates to a uroflowmetry device comprising
  a core unit comprising one or more accelerometers, a capacitive sensor, and a weight sensor;
  a receptacle for collecting urine, operationally coupled to the core unit; and,
  a holder for holding the core unit and the receptacle.

Preferably, the uroflowmetry device as described herein further comprises a core unit as described herein and a receptacle as described herein, wherein
  the accelerometer is configured for detecting the orientation of the core unit and the receptacle with respect to the horizontal plane;
  the accelerometer is configured for detecting shocks;
  the urine detector is configured for detecting the presence of urine in the receptacle;
  the weight sensor is configured for detecting the weight of the urine in the receptacle, and for detecting the rate at which urine flows into the receptacle; and,
  the weight sensor is configured for detecting when micturition is over.

In an additional aspect the present invention also relates to a computer-implemented method for performing a uroflowmetry test using a uroflowmetry device comprising a core unit, a urine receptacle, device activation means, volume detection means, and test validation means, the method comprising the steps:
  a. receiving a signal $S_{rda}$ from the device activation means;
  b. in response to the signal $S_{rda}$ received from the device activation means, sending a signal $S_{sud}$ to the urine volume detection means, the signal $S_{sud}$ encoding for an instruction for turning on the urine volume detection means;
  c. receiving a signal $S_{rud}$ from the urine volume detection means, wherein the signal $S_{rud}$ encodes the urine volume and/or flow rate during a uroflowmetry test;
  d. receiving a signal $S_{rtv}$ from the test validation means, wherein the signal $S_{rtv}$ encodes for either a positive indication or a negative indication; and, e. when the signal $S_{rtv}$ from the test validation means encodes a positive indication, executing the step: sending the signal $S_{rud}$ from the urine volume detection means to a communication module.

Preferably, the computer-implemented method as described herein provides that the uroflowmetry device comprises urine presence detecting means, the method further comprising the steps:
 aa. in response to the signal received from the device activation means, turning on the urine presence detection means; and,
 ab. receiving a signal from the urine presence detection means, the signal encoding the presence of urine;
wherein step b is executed after receiving the signal from the urine presence detection means.

Preferably, the computer-implemented method as described herein provides that the uroflowmetry device is a uroflowmetry device as described herein.

Preferably, the device activation means comprise a capacitive proximity sensor, the urine detector, and/or the accelerometer; wherein the urine volume detection means comprise the weight sensor; and wherein the test validation means comprise the accelerometer.

In an additional aspect the present invention also relates to a computer-implemented method for performing a uroflowmetry test comprising the steps:
 m. receiving a user identification sequence;
 n. receiving a data stream comprising uroflowmetry data, wherein at least part of the data stream is obtained using a method as described herein; and,
 o. displaying the data stream comprising uroflowmetry data on a screen.

BRIEF DESCRIPTION OF THE DRAWINGS

The following description of the figures of specific embodiments of the invention is merely exemplary in nature and is not intended to limit the present teachings, their application or uses. Throughout the drawings, corresponding reference numerals indicate like or corresponding parts and features.

Figure 1:
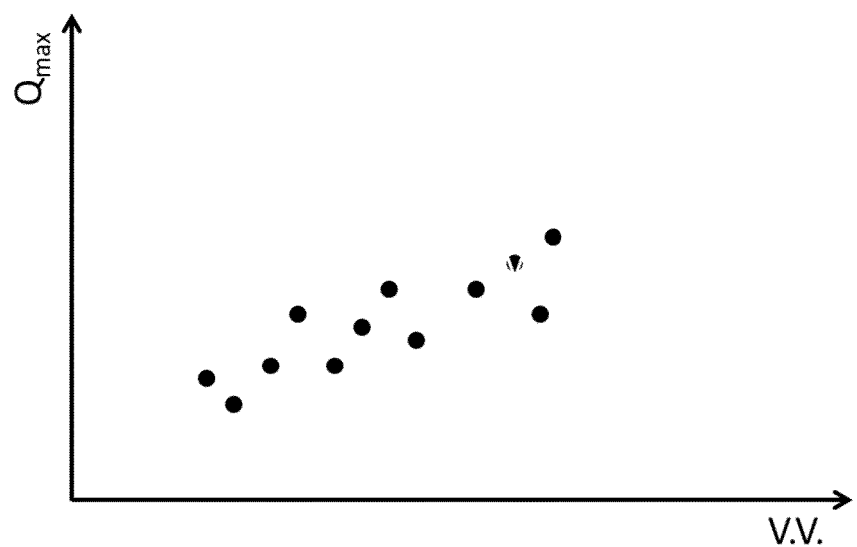
FIG. 1 shows a schematic representation of uroflowmetry measurement data comprising maximum flow rate ($Q_{max}$) versus voided volume (V.V.) data pairs.

Throughout the figures, the following numbering is adhered to: system—100; patient hardware—200; personal computing device—210; temporary communication link—215; core unit—220; communication module—221; processor—222; device activation means—223; urine volume measurement means—224; test validation means—225; energy source—226; cloud-based web service—300; user documentation—310; communications barrier—315; interface portal—320; server hosting a dedicated software portal—400; fiware—450; caregiver hardware—500; laptop computer—510; tablet computer—520; server hosting an electronic health record (EHR)—600; uroflowmetry device—700; receptacle—710; holder—720; seat—730; funnel (urine guide)—740; load cell—810; bracket—820; flexible seal—830; rim—831; leg—832; seal bottom—833; printed circuit board (PCB)—840; top housing—850; button—860; bottom housing—870; lid—880; screw connection—890; screw connection—891; urine weight force indicator—900; indicator of pull force on load cell—910; indicator of force on flexible seals—920; pee hat—1010; pee hat rim—1011; pee hat holder—1012; cup—1020; handles—1030.

DETAILED DESCRIPTION

The present invention will be described with respect to particular embodiments but the invention is not limited thereto but only by the claims. Any reference signs in the claims shall not be construed as limiting the scope thereof.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" when referring to recited members, elements or method steps also include embodiments which "consist of" said recited members, elements or method steps.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within the respective ranges, as well as the recited endpoints.

All documents cited in the present specification are hereby incorporated by reference in their entirety.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

This invention relates to devices, systems, and methods related to the field of uroflowmetry. In particular, in some aspects, the present invention includes a uroflowmetry device comprising a receptacle and a core unit. The receptacle and core unit are configured such that the receptacle is mountable on the core unit, which might be accomplished, for example, by providing the core unit with a flat top and providing the receptacle with a flat bottom, both having a similar size and shape. In particular embodiments, the receptacle and the core unit can be connected to each other; preferably the connection is a reversible connection such as a snap connection or a connection established by means of one or more screws. In particular embodiments, the reversible connection comprises a holder, as described in more detail later on.

In particular embodiments, the receptacle comprises a funnel and a pot. During normal use of a uroflowmetry device provided herein, the funnel is positioned above the pot, and the funnel is configured for receiving urine and directing the urine to the pot.

The core unit comprises a plurality of integrated sensors. In very general terms, the plurality of integrated sensors is configured for sensing the environment of the core unit.

In particular, the recitation "configured for sensing the environment of the core unit" is accomplished by integrating sensors in the core unit.

Preferably, the one or more sensors comprise a capacitive sensor configured for detecting the presence of urine in a receptacle which is mounted on the core unit. In particular, the capacitive sensor is preferably configured for detecting the onset of urination in a receptacle, when the receptacle and the core unit are both part of a uroflowmetry device.

Preferably, the one or more sensors comprise a weight sensor configured for detecting the amount of urine present in the receptacle when it is mounted on the core unit.

Preferably, the one or more sensors comprise an accelerometer, preferably a 3D accelerometer. The accelerometer detects the direction of gravity and accordingly allows the detection of the orientation. Preferably, the accelerometer is configured for detecting the orientation of the core unit and/or the receptacle, a horizontal position of the core unit and/or the receptacle being desirable in order to obtain reliable uroflowmetry measurements. Preferably, the accelerometer is configured for cancelling out movement-related artefacts caused by movement of the receptacle during urination. In particular, the accelerometer measures lateral acceleration and uses movement cancellation filters (digital signal processing) to cancel out particular movement artefacts. Alternatively to the cancelation of the measurement the measurement can also be flagged as invalid. Preferably, the accelerometer is configured for detecting falling of the core unit; recalibration of the weight sensor in the core sensor might be necessary after a fall, such that fall-detection and subsequent recalibration may be efficient means for avoiding faulty calibration-related errors after a fall of the core unit.

The term "lateral" as used herein generally refers to a direction parallel to the weight sensor's load bearing surface. During normal use of the uroflowmetry device, a lateral direction generally corresponds to a horizontal direction within a margin of error of 10.0°, preferably 5.0°, more preferably 1.0°.

Preferably the one or more sensors comprise a capacitive sensor. The capacitive sensor is configured for detecting when urination takes place into the receptacle. This may be useful for turning on the weight sensor only after urine has been detected, which may yield significant energy savings. Typically the capacitive sensor for detecting urination comprises a plurality of standard capacitive sensing electrodes (about ~1 cm in size) positioned throughout the area below the top plastic shell of the core unit. Generally, the capacitive sensing electrodes typically have an area of 1 to 3 $cm^2$.

Preferably, the one or more sensors comprise a presence sensor, for example another capacitive sensor and preferably a capacitive proximity sensor. The presence sensor may be configured for detecting the presence of a patient in the vicinity of the core unit, preferably a proximity of up to 20 cm. Typically the capacitive proximity sensor comprises (circular) electrodes with a diameter of about 10 to 12 cm. In general, the capacitive proximity sensor typically comprises an electrode having an area of about 10 to 15 $cm^2$.

Preferably, the core unit and the receptacle may be configured for communicating via an NFC module/NFC tag pair, wherein the NFC module is incorporated in the core unit and the NFC tag is incorporated in the receptacle, and the NFC tag may comprise a receptacle identification code which encodes a unique identification number of the receptacle. Providing a communication link between core unit and receptacle, for example via an NFC module/NFC tag pair, may be particularly useful for uniquely identifying a receptacle placed on the core unit.

Equivalently, alternative communication standards may be used for providing a communication link between the core unit and the receptacle.

The core unit may further comprise a communication module, wherein the communication module is configured for communicating with a personal computing device. The personal computing device may be, for example, a smartphone or tablet which belongs to a patient, a family member thereof, or a guardian thereof.

Furthermore, the core unit may be configured for communicating with caregiver hardware, e.g. a urologist's computer, by means of a communication link. The communication link may be established by means of a cloud-based web service and a server hosting a dedicated software portal, as detailed in the examples. The caregiver hardware may be configured for generating a report based on the information sent by the core unit through the communication link. The report typically comprises information regarding the amount of measurements, the frequency and the maximum flow rate (Qmax) versus voided volume (V.V.) data for all measurements in a single graph, allowing easy analysis of the data.

In a first aspect, the present invention comprises a core unit of a uroflowmetry device, the core unit comprising at least
- an accelerometer (such as e.g. ST Microelectronics LIS3DH or Invensense MPU-6500);
- a urine detector;
- a weight sensor (such as e.g. Tedea Huntleigh 1002)
- a communication module (such as e.g. Atmel Winc3400 Wifi+Bluetooth Module);
- a microprocessor (such as e.g. Atmel Sam L21) and,
- an energy source (such as e.g. 2×AAA batteries)

In general, uroflowmeters comprising a core unit provided herein allow robust operation with minimal energy use. More broadly, uroflowmeters comprising a core unit as provided herein are suitable for home use. The terms "uroflowmeter" and "uroflowmetry device" as used herein are mutually interchangeable.

The recitation "robust operation" as used herein refers to the ability of the core unit to detect faulty measurements, thereby reducing the risk of incorrect diagnosis.

In particular, robust operation may be accomplished as follows: The core unit's accelerometer allows the detection of shocks during uroflowmetry measurements. Shocks may occur, for example, when a patient's leg accidentally hits a receptacle during a uroflowmetry measurement, or for example when an infantile patient hops on a micturition chair comprising a core unit provided herein. Such shocks may compromise uroflowmetry measurements, and accordingly, there is a need for detecting them and for labelling the uroflowmetry measurements during which shocks were detected as invalid measurements, and/or as measurements which require further attention. Invalid measurements should not be relied upon as a basis for diagnosis by medical professionals. Measurements which require further attention should undergo additional scrutiny during their interpretation in order to mitigate or reduce the risk of faulty diagnosis. Additionally, also other measurements such as a mechanical overload protection of the load cell, waterproofness of the core unit and battery reverse polarity protection may contribute in the robust operation.

In particular, minimal energy use may be accomplished as follows: preferably, the accelerometer is configured for detecting lateral displacements and the accelerometer is always on. The recitation "always on" indicates, when referring to a sensor, a continual measurement of a parameter, and in case of an accelerometer, the recitation "always" on refers to continual acceleration measurements. When the accelerometer detects a displacement, preferably when the accelerometer detects a lateral acceleration, the urine detector is switched on, wherein the recitation "switched on" indicates a state in which a sensor is configured for continually sensing. The recitation "switched off" is the antonym of the recitation "switched on". When the urine detector detects urine, the weighted sensor is turned on. This particular configuration saves energy in standby mode and accordingly, the core unit can be used longer without requiring maintenance. In particular, the energy savings are accomplished because the accelerometer consumes less power than the urine detector, and the urine detector consumes less power than the weight detector.

Accordingly, one of the core unit's components is the accelerometer. The accelerometer allows the uroflowmeters comprising it to be suitable for home use. Making uroflowmeters suitable for home use generally involves achieving at least the following objects: enhancing the reliability of the uroflowmetry device, saving energy, and minimizing the amount of steps a user has to perform in order to make a successful measurement.

By incorporating the accelerometer, the reliability of uroflowmetry devices is enhanced. As previously mentioned, enhancing the reliability of uroflowmetry devices involves detecting the orientation of the core unit with respect to the horizontal plane, and it involves detecting shocks.

By incorporating the accelerometer, energy savings are achieved. Energy savings are particularly important in the context of battery-powered uroflowmetry devices: high energy consumption would require frequent battery changes, which in turn increase the chance of missed measurement opportunities. After all, when a user notices that battery charging needs to happen when micturition is due, the battery charging may be deferred until after micturition has occurred. Furthermore, changing and/or charging batteries is a cumbersome activity, which results in a reduced user experience, which may in turn reduce user compliance.

The accelerometer also aids in minimizing the amount of steps users have to perform in order to make a successful uroflowmetry measurement. In particular, the accelerometer allows automatically switching on the device when a lateral displacement is sensed. Minimizing the amount of steps a user has to perform in order to make a successful uroflowmetry measurement generally has a beneficial effect on user adoption and compliance.

In some embodiments, the core unit comprises a printed circuit board (PCB) on which are arranged one or more components chosen from the list comprising the accelerometer, the urine detector, the communication module, and the microprocessor.

In some embodiments, the core unit comprises a bracket. The bracket may serve to transfer external forces, e.g. forces due to the weight of urine, to the weight sensor. In particular, the bracket may be mechanically connected to one or more flexible seals extending through the outer hull of the core unit. Preferably, the bracket is connected to the one or more flexible seals by means of a rigid leg comprised in each one of the one or more flexible seals. The one or more flexible seals may be elastically connected to the outer hull of the core unit, preferably by means of an elastic rim. Accordingly, the outer hull can move independently from the bracket. The terms "housing" and "hull" as used herein can be used interchangeably.

The terms "weight sensor" and "load cell" as used herein are used interchangeably. In some embodiments, the weight sensor comprises a strain gauge.

In some embodiments, the weight sensor comprises a proximal side and a distal side. The proximal side of the weight sensor is mechanically connected to the bracket and the distal side is mechanically connected to the outer hull. Accordingly, mechanical forces on the core unit can be efficiently transferred to the weight sensor. In some embodiments, the mechanical connections are accomplished by means of screws.

Accordingly: in some embodiments, the core unit comprises an outer hull, one or more flexible seals, a bracket, and a weight sensor, the one or more flexible seals comprising a flexible rim and a rigid leg, the weight sensor comprising a proximal side and a distal side, the weight sensor further comprising a strain gauge between the proximal side and the distal side, wherein
   the flexible rim elastically connects the flexible seals to the outer hull;

the rigid leg rigidly connects the flexible seals to the bracket;

the rigid leg preferably protrudes out of the outer hull;

the bracket is mechanically connected to the proximal side of the weight sensor;

the outer hull is mechanically connected to the distal side of the weight sensor.

In this configuration, the core unit can be used to record the weight of urine in uroflowmetry measurements in an efficient way.

In some embodiments, the rigid leg is flattened. This can enhance the load-bearing capabilities of the rigid leg, thereby enhancing the accuracy of the uroflowmetry measurements.

In some embodiments, the flexible rim is U-shaped. In this way, the influence of the flexible seal on the force transferred through the rigid leg is minimized. This enhances the accuracy of uroflowmetry measurements.

The legs of the flexible seals are generally rigid and stiff compared to their rims, thereby limiting the movement of the bracket compared to the movement of the outer hull during uroflowmetry measurements.

Additional energy savings may be accomplished by providing "end-of-urination" detection. In particular, the weight sensor and the urine detector are switched off when the end of urination is detected. In particular, end-of-urination may be detected by one of the following possibilities. First, "end-of-urination" detection occurs when a sudden and strong decrease in weight is detected by the weight sensor. This indicates urine disposal. Second, "end-of-urination" detection occurs when the weight sensor detects a constant weight for a specified time period, preferably at least 20 s, for example at least 30 s or at least 40 s. A detection of constant weight for such a specified time period may occur, for example, when a user forgot to empty the receptacle.

Furthermore, uroflowmetry systems comprising a core unit according to the present invention may allow for easily and reliably gathering of data from home uroflowmetry measurements. This may enhance the accessibility of certain urological tools, for example, it may facilitate the construction of $Q_{max}$ versus V.V. graphs, an example of which is schematically shown in FIG. 1, wherein $Q_{max}$ is the maximum urine flow rate during urination, and V.V. is the voided volume.

Additionally, uroflowmetry systems comprising core units according to the present invention allow executing uroflowmetry measurements with a very limited amount of steps. This may enhance user adoption and user compliance, which may both be enhanced by limiting the amount of steps which have to be executed by users.

In general, a core unit provided herein may offer robust and energy efficient operation of home uroflowmetry systems.

Furthermore, the weight sensor is preferably configured for measuring the flow rate of urine as a function of time during uroflowmetry measurements. The resulting measurement data may be captured by the microprocessor where they are encrypted and further sent to the communication module. The communication module may further send the encrypted measurement data to patient hardware, and/or caregiver hardware as detailed elsewhere herein.

Preferably, the core-unit is waterproof, preferably with a waterproof IP rating of at least IP54. This enhances the reliability of uroflowmetry devices comprising the core unit.

In some embodiments, the core unit comprises a water proof hull. In particular, the water proof hull is preferably compliant with the requirements for an IP 65 and/or an IP 66 rating.

IP 65-compliant enclosures are able to protect against water jets. In particular, water projected by a nozzle (6.3 mm) against the enclosure from any direction has no harmful effects under the following test conditions: duration of at least 15 minutes, 12.5 liters per minute, 30 kPa pressure at a distance of 3 m.

IP 66-compliant enclosures are able to protect against powerful water jets (12.5 mm nozzle). In particular, water projected against the enclosure from any direction does not have any harmful effects under the following test conditions: duration of at least three minutes, 100 litres per minute, pressure of 100 kPa at a distance of 3 m.

Furthermore, the hull preferably withstands disinfectants chosen from the list comprising: 70% alcohol, quaternary ammonium compounds, hydrogen peroxide, chlorine oxide, and/or disinfecting wipes.

In some dimensions the hull may be cleaned with water under a tap and may be subsequently disinfected with wipes.

The hull may comprise several components which are joined via one or more physical and/or chemical joining techniques. For example, overmolding featuring a chemical connection between different materials may be used. Accordingly, contamination between different materials constituting the hull may be efficiently avoided.

In some embodiments, the core unit's hull comprises a top housing including a bottom, a bottom housing, and a lid.

The urine detector is a detector which is configured for detecting the presence of urine in a receptacle and/or the onset of urination into a receptacle, when the receptacle and the core unit are part of a uroflowmetry device. In particular embodiments, the urine detector is a capacitive sensor. In particular the capacitive sensor comprises a plurality of capacitive sensing electrodes. By comparing the data from the capacitive sensing electrodes to each other the presence of liquids can be detected.

In particular embodiments, the energy source may comprise one or more batteries.

In particular embodiments, the core unit may comprise an NFC module. Alternatively also other wireless technologies such as but not limited to Enocean, Zigbee or Bluetooth may be used.

In particular embodiments, the thickness of a core unit is between at least 1 cm and at most 5 cm, between 1.5 and 3 cm, preferably about 2 or 2.5 cm. Such thin core units are particularly useful for use in uroflowmeters for children. Uroflowmeters for children ideally have a low height such that their ergonomical use by children is facilitated.

The term "thickness" as used herein, when referring to a core unit, refers to the dimension of the core unit in the vertical dimension when the core unit is in a lying position. The core unit generally being approximately disk-shaped, the thickness of the core unit corresponds to the usual interpretation of the term "thickness" when referring to the thickness of a disk.

In particular embodiments, the width of a core unit ranges between 8 and 20 cm, and preferably between 12 and 15 cm.

In particular embodiments, the core unit further comprises a proximity sensor.

In particular embodiments, the proximity sensor comprises another capacitive sensor.

Preferably, the proximity sensor is configured for detecting the vicinity of a person, for example a patient.

In particular, the proximity sensor contributes to the core module energy savings; the proximity sensor may be always on if the core unit is placed horizontally. When the proximity sensor detects a person in its vicinity, the urine detector is turned on. In this sense, the proximity sensor fulfils a role which is complimentary to one of the roles of the accelerometer (i.e. the role of detecting lateral displacements). As before, once the urine detector detects urine, the weight sensor is turned on. As such, the incorporation of a proximity sensor in the core unit may confer energy savings as the energy use of proximity sensors is generally less than the energy use of urine detectors, and the energy use of urine detectors is generally less than the energy use of weight detectors.

In particular embodiments, the core unit further comprises an inductive power module.

The inductive power module in the core unit may be used for transferring electrical power to another device. In particular, the other device comprises comprise an inductive power module as well, which is configured for inductive coupling with the inductive power module of the core unit. The power received by the inductive power module of the other device can be used for powering electronic components in the other device. In particular, the other device may be a receptacle, as described in more detail later on.

In particular embodiments, the core unit may comprise a memory module.

Preferably, the memory module is configured for storing more than 50 uroflowmetry measurements.

The memory module may be particularly useful when the core unit is used in places without wireless internet, or in places having only a poor wireless internet connection. Also, the memory module is particularly useful when the communication module of the core unit is configured to transfer uroflometry data to a cloud-based web service through the personal computing device. A wireless connection between personal computing device and core module may not always be available. If no memory were present in the core unit, data loss might occur when uroflowmetry measurements are taken when no wireless connection between core unit and personal computing device is available. A memory in the core unit allows temporarily storing uroflowmetry data when no wireless connection is available. Accordingly, loss of data can be prevented by providing an internal memory in the core unit.

The wireless internet connection may be, for example, a wifi connection. In such circumstances, the memory module may be configured to store uroflowmetry measurements, for example more than 100 uroflowmetry measurements. When the core unit is brought into an environment in which wireless internet access is available, the uroflowmetry measurements may be transferred from the memory module to caregiver hardware and/or to a personal computing device, e.g. a personal computing device belonging to a patient, their parent, or belonging to a patient's guardian. The concepts "caregiver hardware" and "personal computing device" are further explained below.

In particular embodiments, the accelerometer is configured for:
  detecting an acceleration in a lateral direction;
  detecting shocks; and/or
  the accelerometer is configured for detecting the orientation of the core unit with respect to the horizontal plane.

This overall configuration of the accelerometer allows for a more energy efficient and more robust operation of the core unit, wherein the recitation "more robust operation" refers to the capability of detecting faulty measurements.

In particular, as discussed before, the incorporation of an accelerometer in the core unit, wherein the accelerometer is configured for detecting acceleration in a lateral direction, unit allows energy savings. In addition, the function of the accelerometer and the proximity sensor provides complementary and/or redundant information to be used for turning on the core unit and/or specific components thereof, such as the capacitive urine detection sensor. The accelerometer in companion with the presence detector provides complementary information to activate the urine detector. Typically the accelerometer provides information about the position of the core unit (e.g. core unit in horizontal position) while the presence detector detects that a person has the intention to use the device, conditions which require the activation of the urine detector.

Furthermore, as discussed before, shock detection enhances the robust operation of uroflowmetry systems comprising a core unit provided herein.

In addition, detecting the orientation of the core unit in the horizontal plane further enhances the robustness of uroflowmetry measurements done with uroflowmetry systems comprising a core unit provided herein and a receptacle. In particular, a core unit preferably comprises a portion which is configured for holding a receptacle in a precisely defined, fixed configuration. Hence, by knowing the orientation of the core unit with respect to the horizontal plane, the orientation of the receptacle with respect to the horizontal plane is known when the receptacle is held by the core unit.

Generally, a uroflowmetry system is first calibrated in a calibration test in which the receptacle has a certain orientation with respect to the horizontal plane. By ensuring that the orientation of the receptacle with respect to the horizontal plane is the same during a calibration test and during subsequent uroflowmetry measurements, the uroflowmetry system's robustness is enhanced.

In particular embodiments, the core unit comprises a waterproof housing, in which at least the accelerometer, the urine detector, the weight sensor, the communication module, the energy source, and optionally the proximity sensor, are embedded.

Accordingly, the electronics in the core unit are protected from moisture ingress and accidental liquid spills, thereby reducing the chance that core units provided herein fail due to human error, or due to less-than-ideal storage conditions.

In particular embodiments, the core unit further comprises a capacitive sensor, wherein the capacitive sensor is preferably configured for detecting the presence of urine.

Accordingly, the capacitive sensor is a specific embodiment of the core unit's urine detector, as recited above.

The capacitive sensor may be particularly useful for detecting the difference between the presence of urine on the weight sensor, and the weight sensor being subject to stray influences. The stray influences may comprise, for example, a patient exerting pressure on the weight sensor with their hands.

In particular, a capacitive sensor may be useful for detecting the difference between the presence of urine on the weight sensor In particular embodiments, the capacitive sensor is configured for detecting the urine volume and/or the flow rate of urine in a receptacle, the receptacle being part of a uroflowmetry system comprising a core unit provided herein. The configuration of the electrodes of the capacitive sensor is used to measure the level of a liquid the container. Based on the shape of the container and the change of liquid level, the flow rate can be calculated as well.

In particular embodiments, the capacitive sensor configured for detecting the urine volume and/or the flow rate of urine in a receptacle is a capacitive sensor different from the capacitive sensor for detecting urine.

In particular embodiments, the core module further comprises a button. Preferably, the core unit comprises a capacitive proximity sensor, a urine detector (preferably a capacitive urine detector), and an accelerometer. Preferably, the button is configured for activating/waking up the core unit for first use and/or when the core unit has not been used for more than a pre-determined amount of time, for example 24 hours. Preferably, the capacitive proximity sensor, the capacitive urine detector, and/or accelerometer is/are configured for activating the core unit when the core unit was used in a uroflowmetry measurement less than a pre-determined amount of time ago. This enables energy savings.

In particular embodiments, the weight sensor is configured for detecting the weight of urine and/or the change of the weight of urine in time. The weight sensor is preferably a load cell sensor.

Using known conversion procedures, the weight of urine and/or the change of the weight of urine in time may be readily converted to key uroflowmetry measurements such as flow rate as a function of time, flow time, time to maximum flow rate, average flow rate, maximum flow rate, voiding time and voided volume. The sampling rate of the weight sensor ranges typically between 5 Hz and 50 Hz, more preferably between 10 Hz and 30 Hz, more preferably between 15 Hz and 25 Hz and for instance 20 Hz.

This aspect and/or particular embodiments thereof may be combined with any other aspect of the present invention and/or any particular embodiments thereof.

In a further aspect, the present invention comprises a receptacle configured for operationally coupling with a core unit provided herein comprising urine analysis sensors for providing a chemical analysis of the urine. This chemical analysis of the urine may include the measurement of the pH (using a pH sensor), the specific gravity of the urine, the detection of proteins in the urine (typically the measurement of the amount of albumin in the urine), the detection of glucose in the urine, the detection of ketones in the urine, the detection of blood in the urine, the detection of leukocyte esterase in the urine, the detection of nitrite/nitrate in the urine, the detection of bilirubin in the urine, and/or the detection of urobilinogen in the urine. In particular embodiments the urine analysis sensors for providing a chemical analysis of the urine comprise at least pH sensors and nitrite and/or nitrate detectors. The measurement of the pH level in urine allows early detection of kidney and/or bladder stones but also general problems in the body can be deduced from the pH level. A nitrate sensor enables the early detection of infections. Preferably, the sensors for providing a chemical analysis of the urine will be integrated in the receptacle.

In particular embodiments, the receptacle comprises an NFC tag. The NFC tag may comprise an identification code of the receptacle. Thus, a receptacle may be uniquely identifiable, which may be useful for, for example, associating a specific receptacle with a specific patient.

In particular embodiments, the receptacle comprises an inductive power module, wherein the inductive power module is configured to receive electromagnetic power through inductive coupling with an inductive power module of a core unit. The inductive power module in the receptacle transfer the received electromagnetic power by means of electrical wiring, e.g. copper wiring, to one or more sensors or other electronic components embedded in the receptacle.

The NFC tag comprised in the receptacle may also link with the NFC reader in the core unit according to the present invention. The NFC reader may transfer power to the NFC tag inductively and open a bi-directional communication channel to it. In particular embodiments the NFC tag in the receptacle is further provided with an electronics board which gets powered through the NFC reader. In a particular embodiment the urine analysis sensors transfer data of the chemical analysis to the core unit via NFC.

This aspect and/or particular embodiments thereof may be combined with any other aspect of the present invention and/or any particular embodiments thereof.

It should be clear that a receptacle without any type of electronics incorporated therein can also be used in the uroflowmetry device according to the present invention.

In a further aspect, the present invention comprises a uroflowmetry device comprising
   a core unit comprising one or more accelerometers, a capacitive sensor, and a weight sensor;
   a receptacle for collecting urine, operationally coupled to the core unit; and,
   a holder for holding the core unit and the receptacle.
   Preferably, the core unit is a core unit provided herein.
   Preferably, the receptacle is a receptacle provided herein.
   More preferably, the core unit is a core unit provided herein and the receptacle is a receptacle provided herein.

In particular embodiments, the core unit is a core unit provided herein and the receptacle is a receptacle provided herein, the device further comprising a holder for holding the core unit and the receptacle, wherein
   the accelerometer is configured for detecting the orientation of the core unit and the receptacle with respect to the horizontal plane;
   the accelerometer is configured for detecting shocks;
   the urine detector is configured for detecting the presence of urine in the receptacle;
   the weight sensor is configured for detecting the weight of the urine in the receptacle, and for detecting the rate at which urine flows into the receptacle; and,
   the weight sensor is configured for detecting when micturition is over.

When used as a verb, the term "micturition" as used herein refers to the act of urination.

When used as a noun, the term "micturition" as used herein refers to human urine.

Detection when micturition is over may occur as indicated above, in the disclosure of the core unit.

Preferably, the holder is configured for forming a reversible connection between the receptacle and the core unit, wherein the reversible connection is optionally chosen from the list comprising: snap connections, and connections comprising a plurality of screws. Preferably the core unit and the receptacle both have a flat surface with a lateral border that centres the receptacle cup on top of the core unit.

In some embodiments, the holder is comprised in a pee hat. In particular, the pee hat comprises a rim and a holder. The rim is configured for positioning the pee hat on a toilet.

The holder is configured for holding a core unit and a receptacle. It comprises a hole in which the core unit fits. Around the hole, there is generally a small edge, on which the outer edge of a core unit can rest, for example on one or more flexible seals.

Note that the terms "receptacle" and "cup" as used herein are used interchangeably.

The pee hat may be used in two configurations: a first configuration for uroflowmetry measurements in a seated position, and a second configuration for uroflowmetry measurements in a standing position.

In uroflowmetry measurements in a seated position, the pee hat is positioned on the toilet with its rim, and the holder is positioned in the toilet bowl. During a uroflowmetry measurement, the core unit and the cup are placed in the holder, and a patient can sit down on the toilet as they would normally do.

In uroflowmetry measurements in a standing position, the pee hat is positioned on the toilet with its rim, and the pee hat is placed with the holder sticking out of the toilet bowl.

In some embodiments, the pee hat comprises a flattened side. At its flattened side, the pee hat's rim is thinner than at the other sides. Accordingly, it can fit in a toilet bowl and still leave some space in the back for stool to pass (during uroflowmetry measurements in a seated position) and/or for emptying the receptacle in the toilet.

In some embodiments, the receptacle comprises handles. These handles allow for easy handling of the cup. Additionally or alternatively, they may function as a spout. In some embodiments, the receptacle comprises handles and the pee hat comprises corresponding holes. Thus, the handles and corresponding holes may function as an overflow.

The uroflowmetry devices provided herein facilitate uroflowmetry measurements. In particular, the uroflowmetry devices provided herein may facilitate multiple uroflowmetry measurements for the same patient. This is especially useful for constructing $Q_{max}$ versus V.V. graphs, an example of which is schematically shown in FIG. 1, wherein $Q_{max}$ is the maximum urine flow rate during urination, and V.V. is the voided volume.

This aspect and/or particular embodiments thereof may be combined with any other aspect of the present invention and/or any particular embodiments thereof.

In a further aspect, the present invention comprises a computer-implemented method for performing a uroflowmetry test using a uroflowmetry device comprising a core unit, a urine receptacle, device activation means, volume detection means, and test validation means, the method comprising the steps:
   a. receiving a signal $S_{rda}$ from the device activation means;
   b. in response to the signal $S_{rda}$ received from the device activation means, sending a signal $S_{sud}$ to the urine volume detection means, the signal $S_{sud}$ encoding for an instruction for turning on the urine volume detection means;
   c. receiving a signal $S_{rud}$ from the urine volume detection means, wherein the signal $S_{rud}$ encodes the urine volume and/or flow rate during a uroflowmetry test;
   d. receiving a signal $S_{rtv}$, from the test validation means, wherein the signal $S_{rtv}$ encodes for either a positive indication or a negative indication; and,
   e. when the signal $S_{rtv}$ from the test validation means encodes a positive indication, executing the step: sending the signal $S_{rud}$ from the urine volume detection means to a communication module.

In particular embodiments, the device activation means are selected from the list comprising accelerometers, capacitive proximity sensor, buttons, a switch and/or a combination thereof.

The device activation means is preferably configured for detecting one or more events which may indicate a uroflowmetry test is upcoming. Preferably, the device activation means comprise a capacitive proximity sensor, a capacitive urine detector, and/or an accelerometer, the details of which are disclosed above, in the disclosure of the core unit. The advantage associated with this particular set of device activation means is that, as discussed above, they may be configured for automatically turning on the urine volume detection means (e.g. a weight sensor), as opposed to requiring patients to turn on the urine volume detection means manually using a button or switch. Accordingly, the number of steps which have to be carried out by a user to perform a uroflowmetry test are minimized, and this generally has a beneficial effect on user adoption and compliance.

In particular embodiments, the device activation means comprises a button and one or more items selected from the list consisting of a capacitive proximity sensor, a capacitive urine detector, and an accelerometer. Preferably, the button is configured for activating/waking up the core unit for first use and/or when the core unit has not been used for more than a pre-determined amount of time, for example 24 hours. Preferably, the capacitive proximity sensor, the capacitive urine detector, and/or accelerometer is/are configured for activating the core unit when the core unit was used in a uroflowmetry measurement less than a pre-determined amount of time ago. This allows energy savings. Preferably, the device activation means comprise an accelerometer and/or a capacitive proximity sensor, as discussed above in the disclosure of the core unit.

Preferably, the volume detection means comprise a weight sensor, as discussed above in the disclosure of the core unit.

Preferably, the test validation means comprise a accelerometer, as discussed above in the disclosure of the core unit.

Preferably, when the test validation means comprise a negative indication, the following steps are executed:
   sending the signal from the urine volume detection means to a communication module; and
   sending the negative indication from the validation means to the communication module.

The communication module may further send the signal from the urine volume detection means and/or the negative indication from the validation means to a personal computing device. Preferably, sending is done over a wireless communication link such as wifi, Bluetooth or the like. Instead of sending the signal to the personal computing device, the signal may be sent directly to a cloud-based web service. When the uroflowmetry data are sent directly to the cloud-based web service, preferably a cellular connection, long term evolution (LTE), Wi-Fi, or low power wide area network (lpwan)-based connection is used. However, preferably, the uroflowmetry data are sent to the personal computing device, which may further sent them to a cloud-based web service.

Details of the personal computing device are discussed above, in the disclosure of the system.

The personal computing device may be configured for executing an app. The term "app" as used herein refers to a computer program product comprising computer-readable instructions which, when loaded on a personal computing device, configures the personal computing device to execute the computer-readable instructions provided herein. In particular, the app may comprise computer-readable instructions for providing feedback to a user of the personal computing device, wherein the feedback comprises a representation of the signal from the urine volume detection means and/or the negative indication form the validation means. In addition, the app may further comprise computer-readable instructions for sending the feedback to caregiver hardware and/or to an electronic health record, wherein the caregiver hardware belongs to a caregiver who monitors the uroflowmetry measurements.

Furthermore, the app may comprise an integrated voiding diary. The voiding diary is typically connected to the uroflow device, allowing the triggering of a notification on the mobile application when a void has taken place. As a result, the patient can be notified and asked to add additional data like such as urge, pain, fluid intake, degree of leakage, etc. Accordingly, it is not required for the patient to register the volume and time of voiding manually because the system as described herein registers these parameters automatically through the uroflow device.

In particular embodiments, the uroflowmetry device used in the method further comprises urine presence detecting means, and the method further comprises the steps:
- aa. in response to the signal received from the device activation means, turning on the urine presence detection means; and,
- ab. receiving a signal from the urine presence detection means, the signal encoding the presence of urine;

wherein step b is executed after receiving the signal from the urine presence detection means.

This particular procedure may further enhance the energy efficiency of the devices provided herein as the energy consumption of urine volume detection means is generally higher than the energy consumption of urine presence detection means.

In particular, the urine presence detecting means may be part of the device activation means, and it may comprise a capacitive sensor, which is described in detail above, in the disclosure of the core unit. In particular, the device activation means may be turned on after detection of acceleration in a lateral direction by a accelerometer, and/or after detection of the nearby presence of a person by a vicinity sensor, as described in detail above, in the disclosure of the core unit.

This aspect and/or particular embodiments thereof may be combined with any other aspect of the present invention and/or any particular embodiments thereof.

In particular embodiments, the uroflowmetry device used in the method is a uroflowmetry device provided herein.

In a further aspect, the present invention comprises a computer-implemented method for performing a uroflowmetry test comprising the steps:
- m. receiving a user identification sequence;
- n. receiving a data stream comprising uroflowmetry data, wherein at least part of the data stream is obtained using a method comprising the steps a, b, c, d, e, f, g, h, k, and l; and optionally steps ea, fa, and fb, as recited above; and,
- o. displaying the data stream comprising uroflowmetry data on a screen.

The recitation "user identification sequence" as used herein refers to identification data of the user during the initial setup of the device.

In particular embodiments, the data stream comprising uroflowmetry data is received by means of a wireless communication module such as a wifi, Bluetooth or other mobile module.

In particular embodiments, the data stream comprising uroflowmetry data is displayed on the screen graphically, for example as a graphical representation comprising a plot of urine flow rate as a function of time. The graphical representation may further comprise numerical and/or graphical indications of the maximum flow rate, the average flow rate, the voided volume, and the voiding time.

In a further aspect, the present invention comprises an integrated urologist portal, wherein the urologist logs in with his account and can access uroflow and voiding diary data of his patients. The portal allows the urologist to conduct additional data analysis with the data received from the patient.

This aspect and/or particular embodiments thereof may be combined with any other aspect of the present invention and/or any particular embodiments thereof.

In a further aspect, the present invention comprises a report based on uroflowmetry data, wherein the uroflowmetry data are generated with the aid of a core unit provided herein, with the aid of a receptacle provided herein, with the aid of a device provided herein, with the aid of a system provided herein, and/or with the aid of a method provided herein.

This aspect and/or particular embodiments thereof may be combined with any other aspect of the present invention and/or any particular embodiments thereof.

While prior art uroflow reports basically consist out of only a single uroflow measurement, the report as described herein exist out of multiple measurements within a 24, 48 or longer cycle (based on how long the patient is measuring himself). Additionally, the report as described herein contains extra uroflow parameters such as the duration of the measurement period, total amount of measurements, amount of failed measurements, maximum voided volume, minimum voided volume and average voided volume which will help the urologist in his diagnosis. The use of multiple measurements also allows additional data analysis like the relationship between Qmax and the voided volume which will help the urologist in his diagnosis.

In a further aspect, the present invention comprises a method for enhancing patient compliance with taking uroflowmetry tests comprising the steps:
- providing a uroflowmetry device provided herein; and,
- providing a sensory queue to a user, wherein the sensory queue is configured for reminding the user to perform a uroflowmetry test and/or to log his liquid intake.

In particular embodiments, the sensory queue may be chosen from the list comprising: text messages, audio signals, and vibrational signals.

Accordingly, patient compliance can be enhanced by reminding users to take uroflowmetry tests and/or to log the liquid intake.

In certain aspects, the uroflowmetry device provided herein may be integrated in a system which facilitates communication between patients and caregivers, e.g. urologists.

Accordingly, the present invention comprises a system comprising a uroflowmetry device provided herein, a personal computing device, a communication link, and caregiver hardware, wherein
- the core unit provided herein and/or the uroflowmetry device provided herein is configured for
  - sending uroflowmetry data to the caregiver hardware through the communication link, and/or
  - receiving informative data such as but not limited to firmware updates and/or inquiries about physical health of device (e.g. the amount of measurements, battery level, memory usage, encryption key exchange); and,
- the personal computing device is configured for
  - sending personal data to the caregiver hardware via the communication link;
  - receiving uroflowmetry data from the caregiver hardware through the communication link.

The term "personal computing device" as used herein refers to an electronic device belonging to a patient, a patient's parent, or a patient's guardian. Suitable, nonlimiting examples of personal computing devices include smartphones, tablets, and personal computers.

The term "communication link" as used herein refers to an information exchange system between two or more devices. In particular, communication links may comprise servers hosting cloud-based web services, and servers hosting dedicated software portals. In some embodiments, the communication link between the core unit and other devices may be routed through the personal communication device.

Such a system may be highly effective means for monitoring patients by means of regularly recurring uroflowmetry tests.

The term "caregiver hardware" as used herein refers to an electronic devices belonging to a caregiver, e.g. a urologist, wherein the caregiver is responsible for follow-up of a patient taking uroflowmetry measurements.

In particular embodiments, the uroflowmetry device and the personal computing device are operationally coupled by means of one of the following procedures. When Bluetooth is not available on both devices, and when wifi is available, the core unit opens up a wifi network, the patient disconnects from his home wifi and connects to the core unit. The core unit uploads its identity encrypted and receives the home wifi credentials. If Bluetooth is available the connection between the patient device and the core unit can be made without disconnecting the patient device from the home wifi and can be maintained after the core unit is connected to the home wifi. The latter allows notifying the patient if the connection of the core unit with the home network was unsuccessful. Also here an important aspect is receiving the identification of the core unit encrypted on the handheld.

In particular embodiments, the personal computing device may be a device chosen from the list comprising smart phones, tablets, and personal computers.

In particular embodiments, the personal computing device may be configured for executing a set of instructions, the set of instructions hereafter termed app, wherein the app comprises:

displaying uroflowmetry data to a user on an electronic display;
providing an electronic voiding diary to a user; and,
prompting a user to fill in the electronic voiding diary.

Furthermore, the app may comprise an integrated voiding diary.

In particular embodiments, the communication link further provides a caregiver, by means of the caregiver hardware, read and/or write access to an electronic health record.

The devices, systems and methods as described herein provide in more reliable measurements with less probability of wrong handling of the device, thereby making the measurements and consequently the diagnosis more robust and less prone to errors. Also, by allowing the patient to urinate in his natural environments (and not e.g. in the doctor's office), the void occurs more naturally thereby increasing the reliability of the results.

This aspect and/or particular embodiments thereof may be combined with any other aspect of the present invention and/or any particular embodiments thereof.

Further provided herein is a computer-implemented method for auto calibrating a load cell in a core unit of a uroflowmetry device. The core unit comprises one or more flexible seals as provided herein. The method comprises the following steps:

1. placing the core unit in a position such that none of the one or more seals touch any solid objects; measuring, by the core unit, the raw signal from the load cell in this position; and storing, in the memory of the core unit, the raw signal from the load cell in this position.
2. placing the core unit inside a dedicated holder such that the flexible seals carry the weight of the core unit. In some embodiments, the dedicated holder is a pee hat.
3. detecting, by the core unit, using the urine detector, when an empty cup is placed on top of the core unit. When this is the case, saving, by the core unit, the raw signal which was detected.
4. retrieving, by the core unit, from the core unit's memory, the core unit's weight and the weight of the cup, and calculating the difference between the raw signal obtained in step 3 and the raw signal obtained in step 1. This difference corresponds to the weight of the core unit plus the weight of the cup.
5. calculating, by the core unit, a gain factor by dividing the difference between the raw values obtained in steps 3 and 1 by the known weight of the sensor and cup.
6. calculating, by the core unit, an offset factor by setting the raw value obtained in step 3 as the 0 g value.

Accordingly, the core unit can be auto calibrated efficiently.

EXAMPLES

Example 1

The present example discloses, referring to FIG. 1, an application of the present invention. In particular, FIG. 1 shows a schematic representation of a maximum flow rate (Qmax) versus voided volume (V.V) graph. Such graphs require many data from many uroflowmetry measurements and may have significant diagnostic value. Uroflowmetry systems according to the present invention allow easy gathering of these data.

Example 2

Figure 2A:
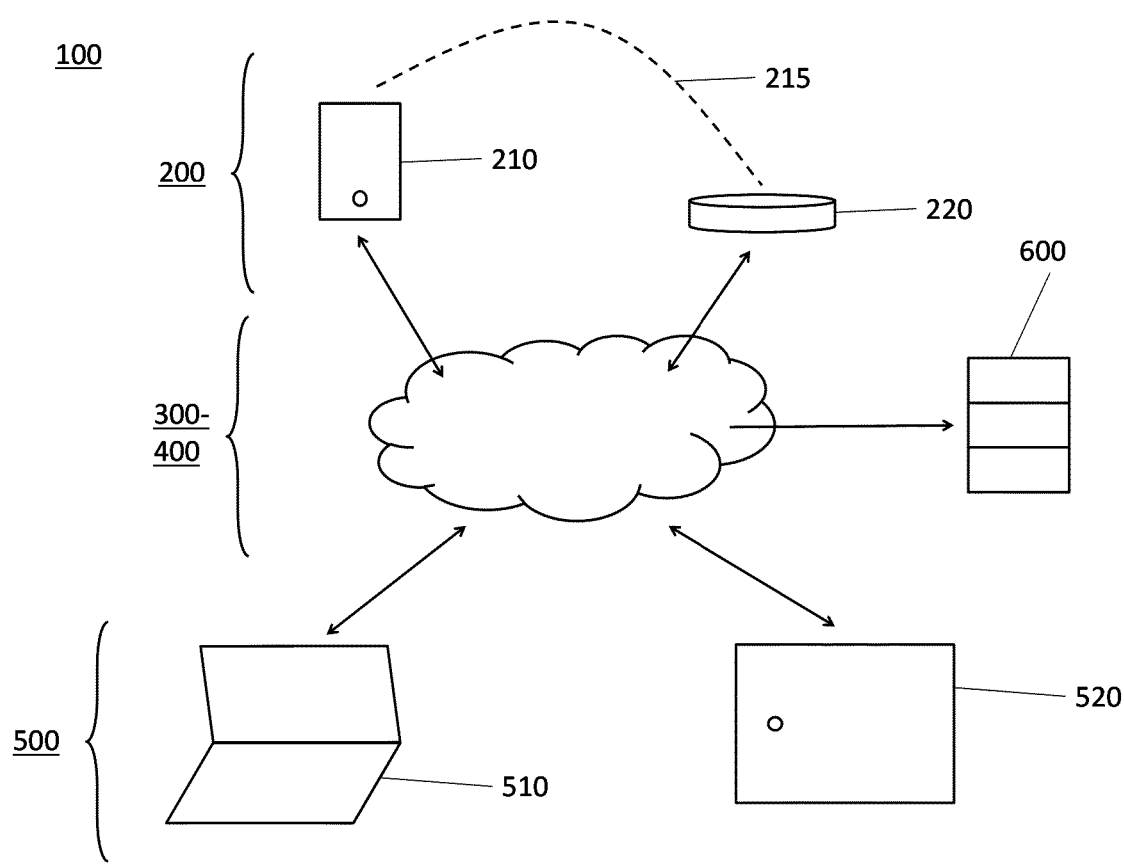
FIGS. 2A, 2B and 2C show different set ups of a system (100) comprising patient hardware (200), a cloud-based web service (300), a server (400) hosting a dedicated software portal, caregiver hardware (500), and a server (600) hosting an EHR.
Figure 2B:
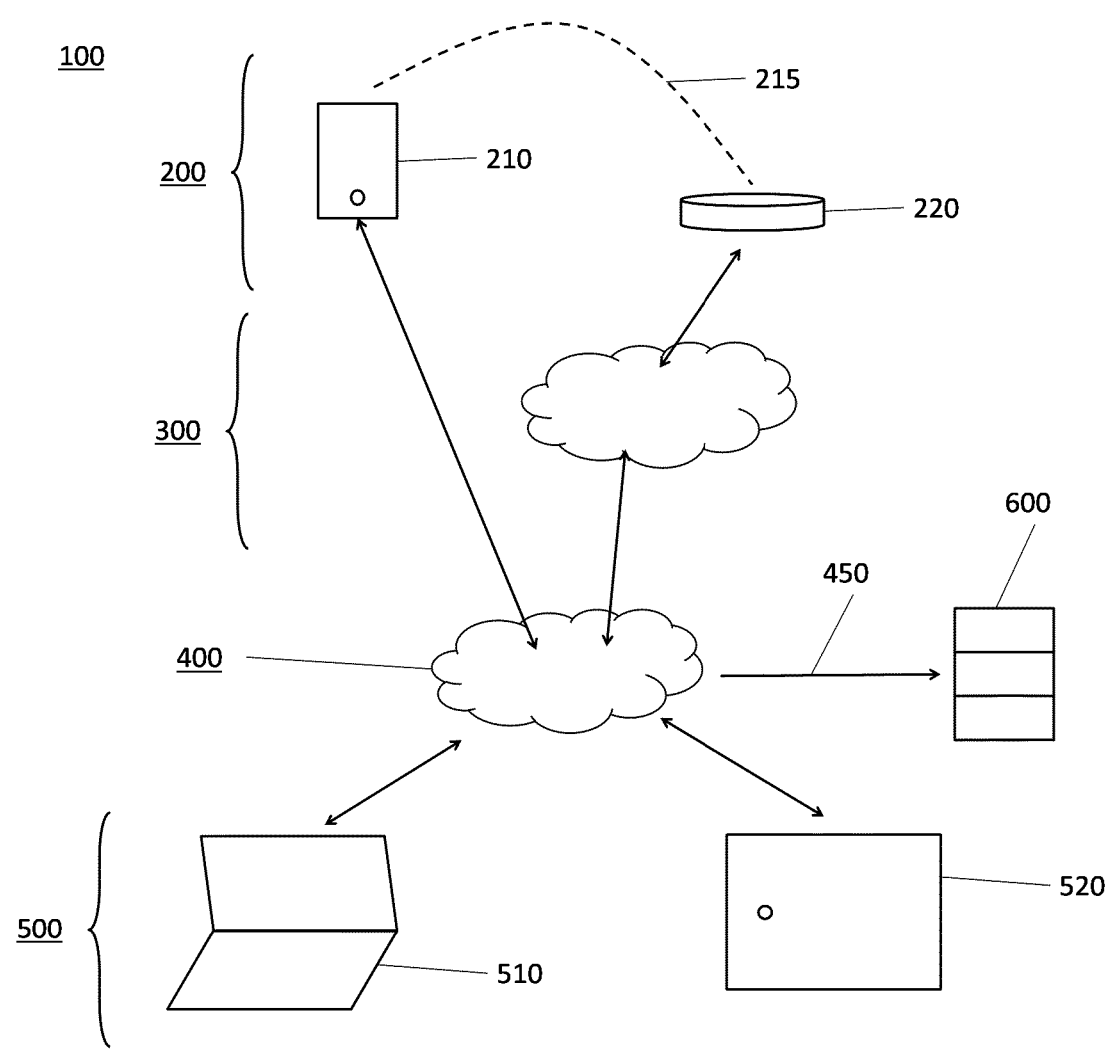
Figure 2C:
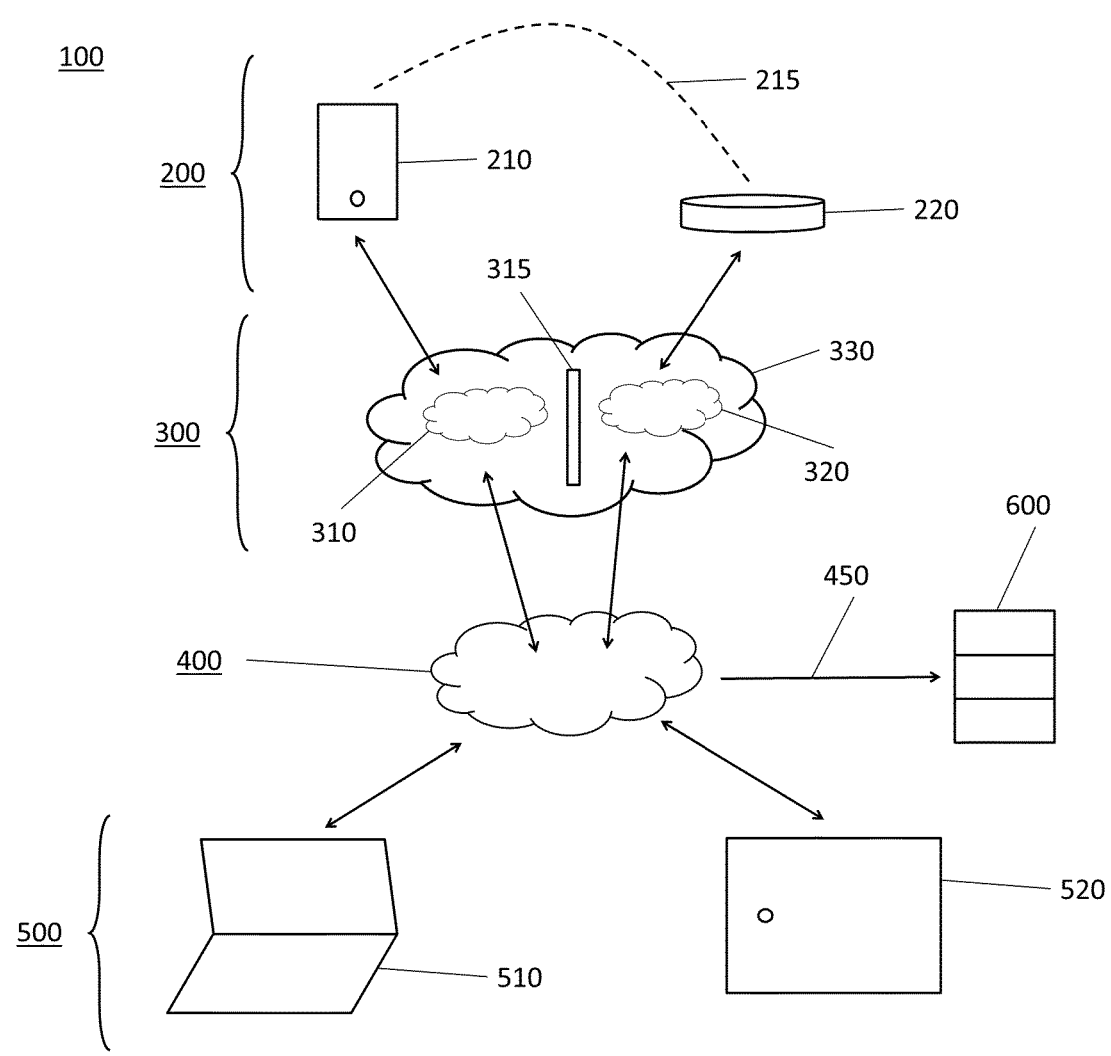

The present example discloses, referring to FIGS. 2A, 2B and 2C, a system (100) comprising patient hardware (200), at least one cloud-based web service (300), a server hosting a proprietary software portal (400), caregiver hardware (500), and a server hosting an electronic health record, or EHR (600).

The patient hardware comprises a smartphone (210) and a core unit (220). The smartphone is configured for running a computer program, hereafter termed app.

The smartphone (210) and the core unit (220) are configured for establishing a temporary communication link (215) between each other during set-up. The temporary communication link (215) is achieved by means of wireless communication according to an IEEE 802.11 or Bluetooth standard. During set-up, the specific core unit is associated with an app running on the smartphone (210). In particular, the association occurs by forwarding the core unit's encrypted product identifier from the smartphone (210) to the web service during setup. Additionally, a user enters their identification data in the app running on the smartphone (210). After setup, the core unit (220) is associated to the user whose identification data were entered in the app.

The identification data and the core unit's encrypted product identifier are subsequently sent by the smartphone (210) to a cloud-based web service (300) where they are stored. When a uroflowmetry measurement is carried out on a uroflowmetry device comprising a core unit (220), the core unit encrypts the uroflowmetry data and subsequently sends them to the cloud-based web service (300). The uroflometry data may either be sent directly to the cloud-based web service (300), or they may first be sent through the smartphone (210). When the uroflowmetry data are sent directly to the cloud-based web service, preferably a cellular connection, Wi-Fi, long term evolution (LTE), or low power wide area network (lpwan)-based connection is used. However, preferably, the uroflowmetry data are sent through the smartphone (210) to the cloud-based web service (300).

The cloud-based web service (300) communicates with a server (400) hosting a dedicated software portal.

The server (400) hosting the dedicated software portal communicates with a server (600) hosting an electronic health record, or EHR, wherein the communication occurs through fiware (450), which is a type of middleware.

The server (400) hosting the dedicated software portal communicates with caregiver hardware (500). The caregiver hardware includes a smartphone (510) and a tablet (520). Different configurations can be used.

As indicated in FIG. 2A, the cloud-based web service (300) and the server hosting a proprietary software portal (400) may be combined into a single web service.

As indicated in FIG. 2B, the server, which hosts the doctor portal, also host the patient information. The patient does not interact with the cloud-based web service (300), but instead everything which is related to patients and doctors goes to the server (400) hosting a dedicated software portal, whereas the cloud-based web service (300) only gathers and stores measurement data and provides them to the server (400) hosting a dedicated software portal when requested.

As indicated in FIG. 2C, when a uroflowmetry measurement is carried out on a uroflowmetry device comprising a core unit (220), the core unit encrypts the uroflowmetry data and subsequently sends them to the cloud-based web service (300), where they are stored in an interface portal (320).

Example 3

Figure 3:
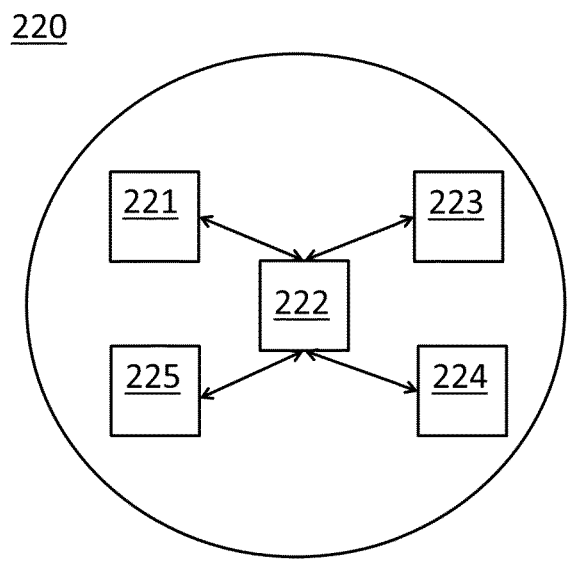
FIG. 3 shows the inner workings of a particular core unit (220).
Figure 4:
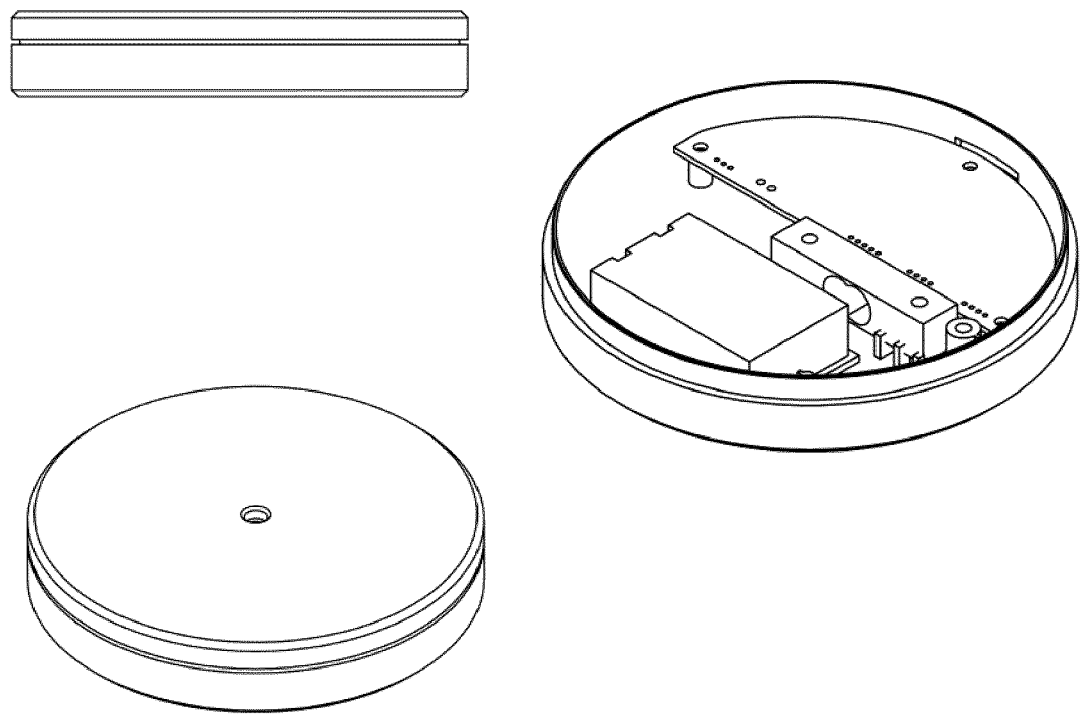
FIG. 4 shows a particular core unit (220).

The present example discloses, referring to FIGS. 3 and 4, a core unit (220) comprising components (221,222,223,224, 225,226). In FIG. 3, reciprocal data flows between the various components (221,222,223,224,225,226) of the core unit (220) are represented by bidirectional arrows. In particular, the components comprise a communication module (221), a processor (222), device activation means (223), urine volume measurement means (224), and measurement validation means (225), and an energy source (226). In particular, the communication module (221) comprises a wifi and/or Bluetooth module; the processor comprises an Atmel SamL21 or ARM-CortexM0+; the device activation means (223) comprise an capacitive proximity sensor, a accelerometer, and a capacitive sensor; the urine volume measurement means (224) comprise a weight sensor; the measurement validation means (225) comprise a accelerometer; and the energy source (226) comprises a battery.

When the core unit is not in use, e.g. when it is stored in a cupboard, the accelerometer of the device activation means (223) is continually operational whereas the other components of the core unit (220) are in standby mode. In case the core unit is placed horizontally, the proximity sensor gets activated as well. As the accelerometer and the proximity sensor consume relatively little power compared to the other components of the core unit, this confers procedure confers energy savings, thereby extending time until the lithium ion battery, which supplies energy to the components (221,222, 223,224,225,226) of the core unit (220), is depleted.

Example 4

Figure 5:
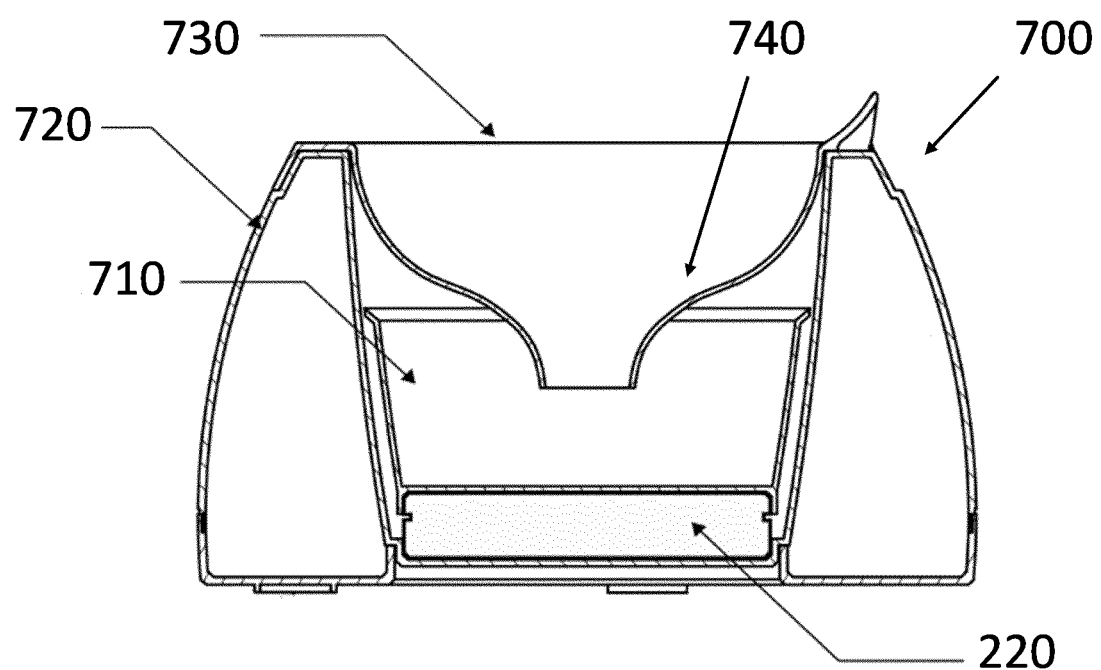
FIG. 5 shows a uroflowmetry device.

The present example discloses, referring to FIG. 5, uroflowmetry device (700) comprising a core unit (220) onto which a receptacle (710) is positioned. A holder (720) encloses the core unit and the receptacle. On top the uroflowmetry device (700) a seat (730) is available. The uroflowmetry device (700) further comprises a funnel (also referred to as urine guide) (740) for guiding the urine in the receptacle.

Example 5

Figure 6:
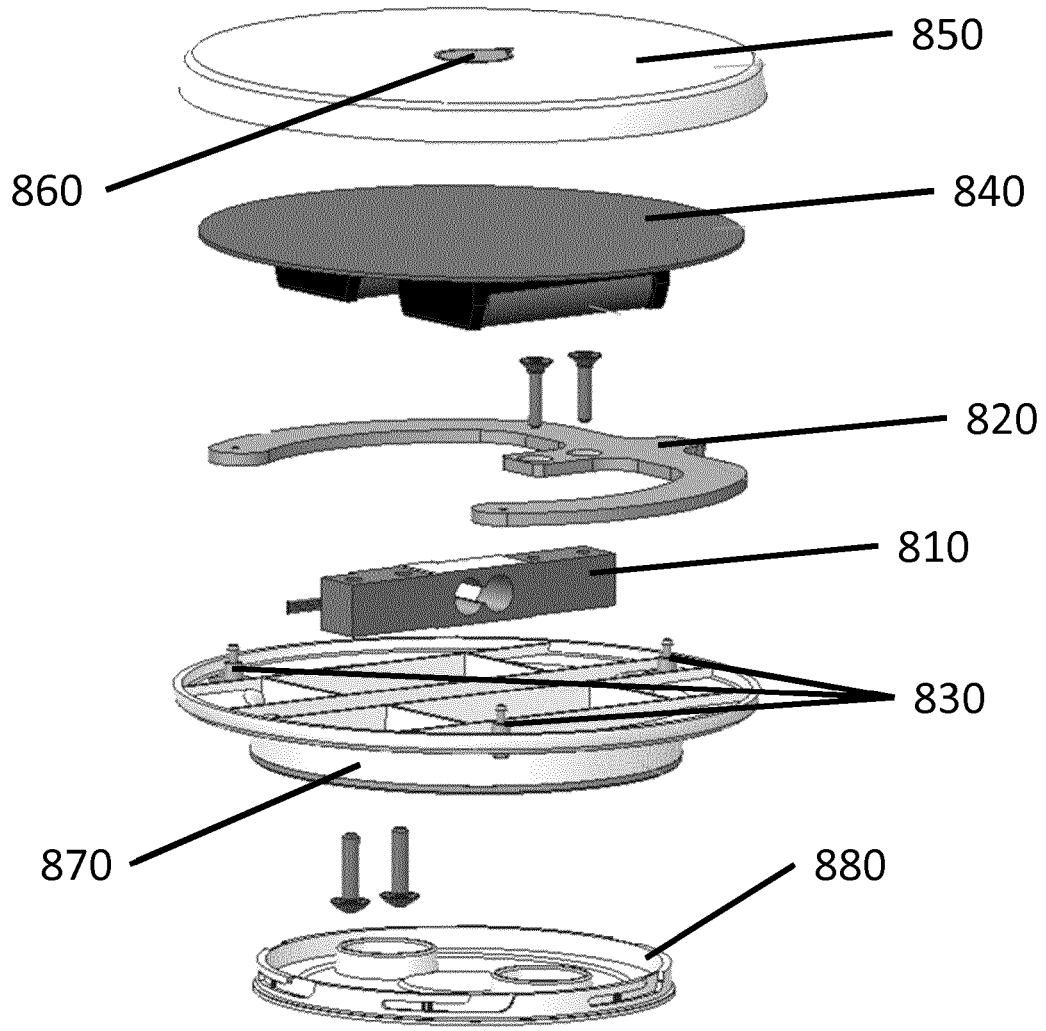
FIG. 6 shows an exploded view of a core unit (220).

In a further example, reference is made to FIG. 6. FIG. 6 shows an exploded view of a core unit (220). The core unit comprises a top housing (850) including a button (860), a bottom housing (870), and a lid (880) which cooperate to form an outer hull and make the core unit (220) water tight, i.e. to allow the core unit to fulfil the requirements for an IP 65-66 rating. The core unit (220) further comprises a printed circuit board (840) comprising a plurality of electrical and electronic components.

The button allows activating the core unit when it has been idle for more than 24 hours and/or when the core unit is first used by a patient. This reduces the core unit's power consumption.

Further comprised in the core unit (220) is a bracket (820). The bracket serves to transfer external forces, e.g. forces due to the weight of urine, to a load cell (810). In order to achieve this object, a mechanical connection between the bracket (820) and the load cell (810) is provided by means of screws.

The load cell (810) is further connected to a bottom housing (870) by means of screws.

The connections between the load cell (810) and the bottom housing (870) on the one hand, and between the load cell (810) and the bracket (820) on the other hand are spaced apart. Between these connections, the load cell (810) is provided with a strain gauge. The operation of the load cell during uroflowmetry measurements is detailed in example 6 and FIG. 7.

Example 6

Figure 7:
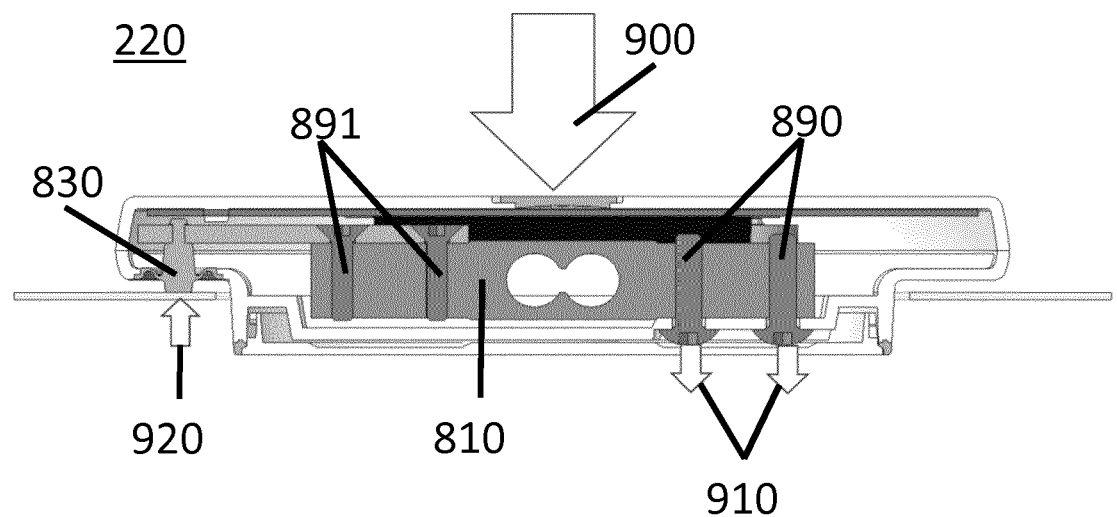
FIG. 7 shows a cross section of a core unit (220).

In a further example, reference is made to FIG. 7. FIG. 7 shows a cross section of a core unit (220). During a uroflowmetry measurement, the weight of urine in a receptacle positioned on the core unit results in a force on the core unit which is indicated by a urine weight force indicator (900).

During a uroflowmetry measurement, the core unit (220) is placed in an appropriate holder (e.g. a pee hat), and the core unit (220) rests on three flexible seals (830).

The three flexible seals (830) are elastically connected to the outer hull of the core unit (220) by means of an elastic rim. The outer hull of the core unit (220) comprises a top housing, a button, a bottom housing, and a lid.

During a uroflowmetry measurement, the force corresponding to the weight of accumulating urine in a recipient placed on the top housing pushes the core unit's hull down. Through a screw connection (891) between bottom housing (870) and load cell (810), this force results in a downward force on the right side of the load cell (810).

On its left side, the load cell (810) is connected to the bracket (820) by means of another screw connection (891). In turn, the bracket is connected to the flexible seals by means of legs. Each leg is a part of a seal, and apart from a leg, each seal also comprises a rim. The seals' legs are relatively stiff compared to the seals' rims. The seals elastically support the outer hull of core unit (220) and they more rigidly support the bracket (820). During the uroflowmetry measurement, the legs efficiently transfer an upward force to the bracket, and the bracket transfers this upward force to the left side of the load cell. This force, along with the downward pulling force exerted by the bottom housing on the right side of the load cell, causes a torque on the load cell. This torque is directly related to the weight of urine in a receptacle positioned on the core unit and is detected by a strain gauge in the load cell.

Example 7

Figure 8:
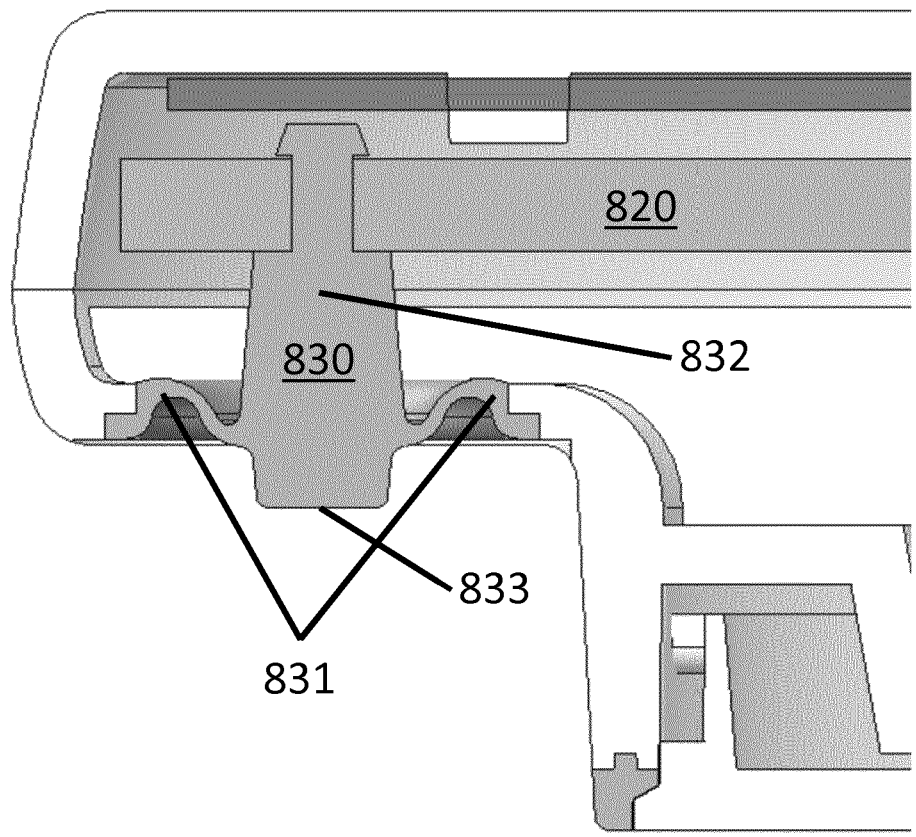
FIG. 8 shows a detailed view of a flexible seal (830).

In a further example, reference is made to FIG. 8. FIG. 8 shows a cross section of a specific seal (830). The seal (830) comprises a leg (832) which is rigid and stiff. The seal further comprises a flexible rim (831). The flexible rim has a u-shape. The u-shape of the flexible rim ensures efficient force transfer to the bracket.

The leg (832) is fixed to the bracket (820). The bottom (833) of the leg protrudes beyond the rim, out of the core unit's outer hull and is flattened. It serves to bear the weight of the core unit during uroflowmetry measurements. The leg (830) is stiff compared to the rim (831) and it rigidly supports the bracket (820).

Example 8

Figure 9:
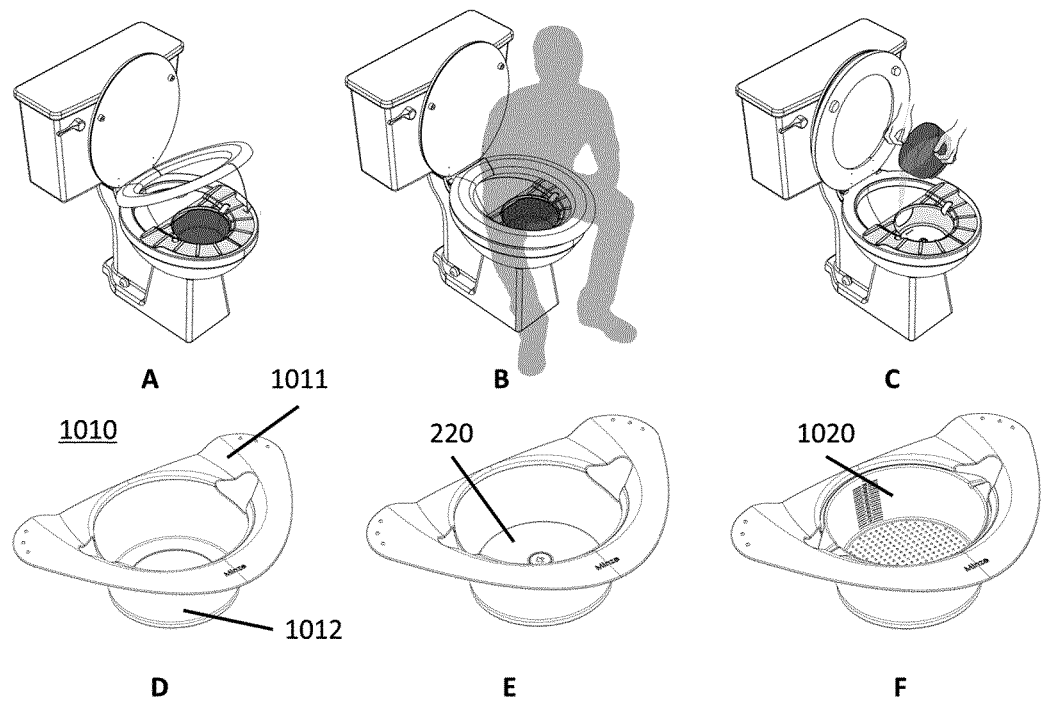
FIG. 9 shows the use and set up of a uroflowmetry device for use in a seated position.
Figure 10:
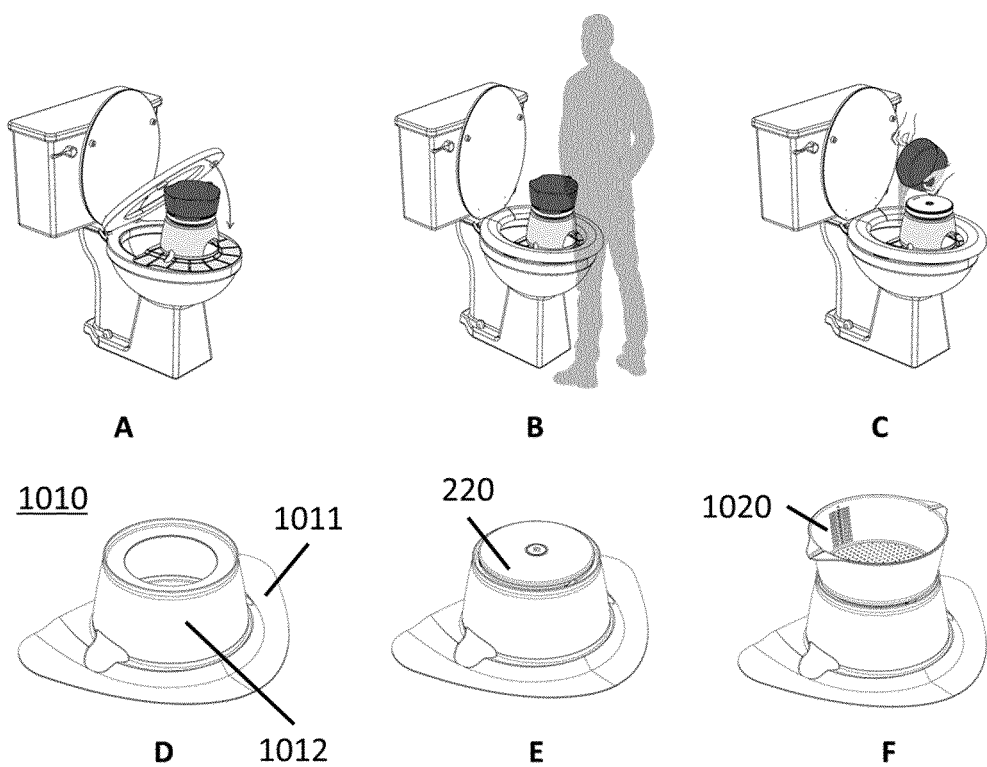
FIG. 10 shows the use and set up of a uroflowmetry device for use in a standing position.

In a further example, reference is made to FIGS. 9 and 10. FIGS. 9 and 10 show exemplary modes of using a uroflowmeter provided herein. The uroflowmeter comprises a pee hat (1010), a cup (1020), and a core unit (220).

In FIG. 9, the uroflowmeter is shown in a set up for use by a sitting patient. In particular, panel A shows the uroflowmeter placed on top of a toilet with its body hanging inside the toilet bowl. A close up of the pee hat (1010) is shown in panel D. The pee hat comprises a rim (1011) for positioning the pee hat on a toilet and the pee hat comprises a holder (1012) for holding a core unit (220) and a cup (1020). For a uroflowmetry measurement, the core unit (220) is placed inside the pee hat (1010) (see panel E), and the cup (1020) in turn is placed on top of the core unit (220) (see panel F). During a uroflowmetry measurement, a patient can sit down on the toilet as they would normally do (panel B). After the uroflowmetry measurement, urine can be emptied into the toilet without removing the pee hat and core unit (panel C): the shape and dimensions of the pee hat (1010) to allow it to fit in the toilet bowl and leave some space in the back for stool to pass and to empty the cup in the toilet.

In FIG. 10, the same uroflowmeter is shown in a different configuration, namely in a set up for use by a standing patient. In this configuration, the pee hat is turned upside down compared to the configuration for use by sitting patients. In particular, panel A shows the uroflowmeter on top of a toilet. The pee hat is placed with its body (the holder (1012)) sticking out of the toilet bowl while the rim (1011) rests on the toilet. A close up of the pee hat (1010) in this configuration is shown in panel D. For a uroflowmetry test (panel B), the core unit is placed on top of the pee hat (see panel E), and the cup is placed on top of the uroflowmeter (see panel F). Near the back of the toilet bowl, some place is left to allow easily emptying the cup in the toilet (panel C). The height increase in this set up compared to the sitting set up of FIG. 9 makes it easier for a standing person to aim during a uroflowmetry measurement.

Example 9

Figure 11:
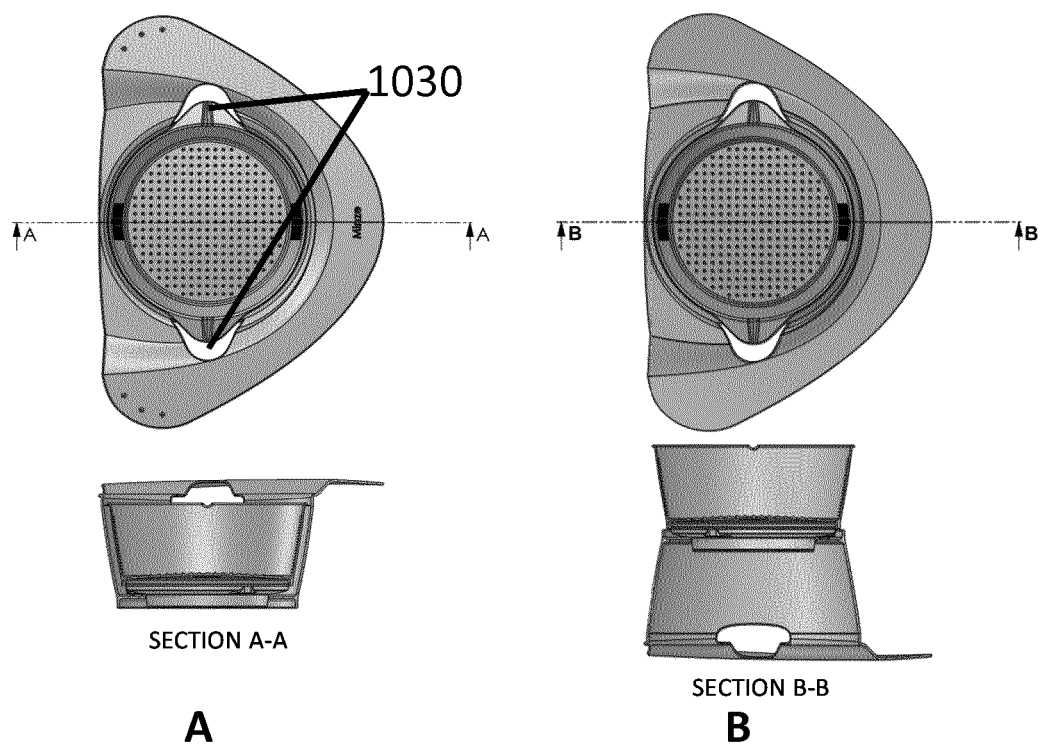
FIG. 11 shows a cross section through a uroflowmetry device.
Figure 12:
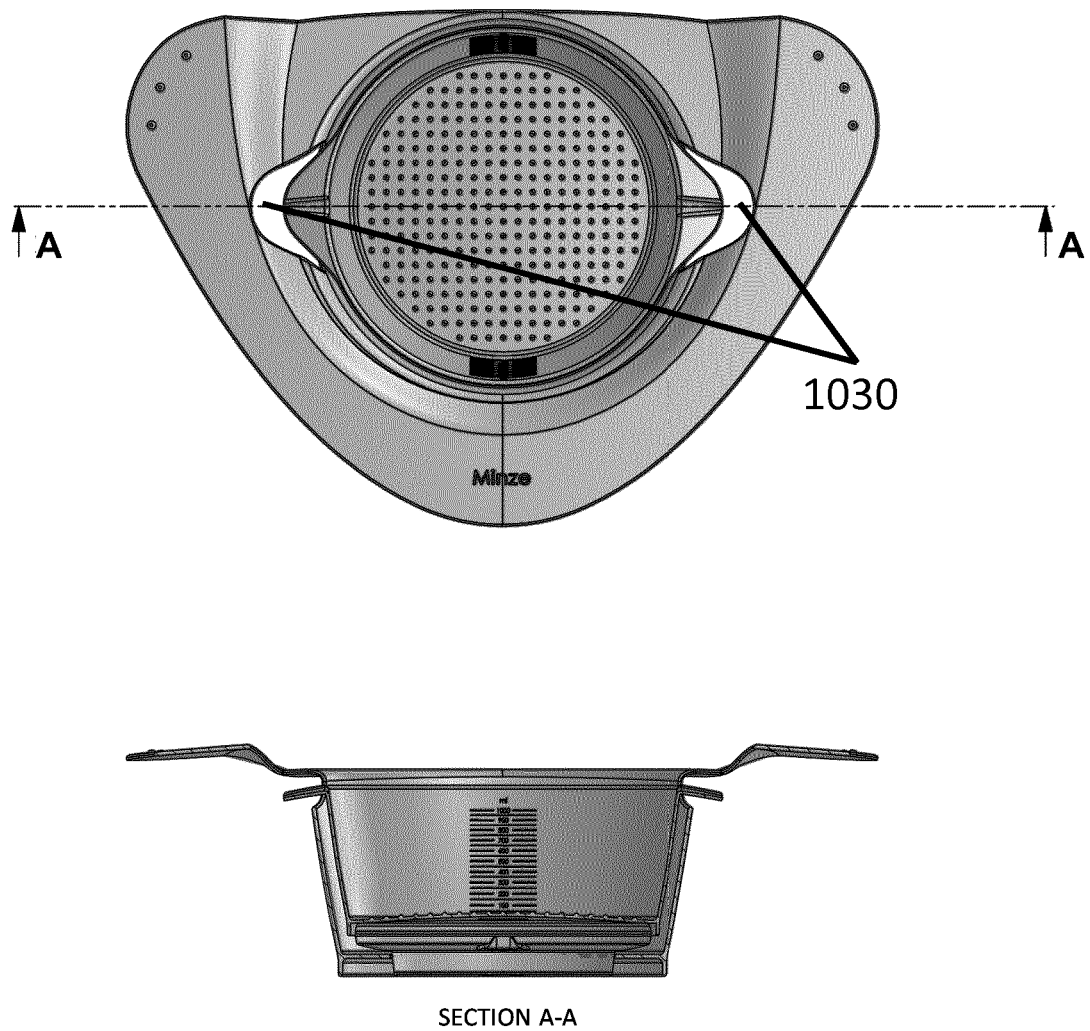
FIG. 12 shows another cross section through a uroflowmetry device.

In a further example, reference is made to FIGS. 11 and 12. FIGS. 11 and 12 show cross sectional views of a pee hat as envisioned herein. The particular shape of the uroflowmeter makes it possible to use either while standing or while sitting down.

In particular, panel A of FIG. 11 shows a cross section of a uroflowmeter ready for use while sitting down whereas panel B of FIG. 11 shows a cross section of the same uroflowmeter ready for use in a standing position.

FIG. 12 shows a different cross section of the uroflowmeter, highlighting its T-shaped cross section when viewed along the section shown in FIG. 12. The particular shape of the uroflowmeter and the corresponding hole in the pee hat make it possible to use the uroflowmeter in both standing and sitting set ups by simply turning the pee hat upside down. Furthermore, the T-shape has several specific benefits: In the set-up for seated uroflowmetry measurements, the cup is provided with ample space in the pee hat such that it can capture a greater volume. In the set up for standing uroflowmetry measurements, the particular shape of the uroflowmetry device makes the set up more stable: the bottom part (smaller diameter) of the core unit ensures that the core unit does not drop out of the pee hat. Furthermore, this lowers the uroflowmeter's centre of gravity.

The cup comprises handles. These handles allow easy handling of the cup. Also, the handles function as an overflow in combination with corresponding holes in the pee hat in the set up for seated uroflowmetry measurements. Furthermore, the handles may function as a pouring spout.

Example 10

In a further example, reference is made to a specific method for auto calibrating the load cell in the core unit. The auto calibration procedure comprises the following steps:

1. When the core unit is not placed inside a dedicated holder, no weight is measured by the load cell since the 3 flexible seals are not touched by any solid objects. The core unit's housing supports all weight and the load sensitive part of the load cell is free hanging. The signal from the load cell in this position is measured by an analog-to-digital converter as a binary raw value, and is used by the core unit as a first point for calibration.
2. Only when the core unit is placed inside a dedicated holder, e.g. a pee hat, the three flexible seals carry the weight of the core unit. The three flexible seals transfer (a part of) the corresponding force, through the bracket, to the load sensitive part of the sensor.
3. The core unit detects, using the urine detector, when an empty cup is placed on top of the core unit. If this is the case, the core unit saves the binary raw value from the analog-to-digital converter and uses it as a second point for calibration.
4. The difference between the raw values obtained in steps 3 and 1 corresponds to the core unit's own weight plus the weight of the cup. The core unit comprises a memory in which its own weight and the weight of the cup are saved.
5. For gain calibration, the core unit divides the difference between the raw values obtained in steps 3 and 1 by the known weight of the sensor and cup. Accordingly, a gain factor is obtained which allows, along with an offset factor, calculating the weight of urine in gram.
6. The offset factor is calculated by setting the raw value obtained in step 3 as the 0 g value. Everything above 0 g equals the weight increase due to urine entering the cup.

The invention claimed is:

1. A uroflowmetry device comprising:
   a core unit comprising one or more accelerometers configured for detecting an acceleration in a lateral direction, detecting shocks and detecting an orientation of the core unit with respect to a horizontal plane, a capacitive urine detector configured for detecting onset of urnination in a receptacle, and a weight sensor configured for measuring flow rate of urine as a function of time in said receptacle;
   said receptacle operationally coupled to the core unit; and,
   a holder for holding the core unit and the receptacle;
      wherein the core unit comprises an outer hull, one or more flexible seals, and a bracket, the one or more flexible seals comprising a flexible rim and a rigid leg, and the weight sensor comprising a proximal side, a distal side, and a strain gauge between the proximal side and the distal side, wherein
         the flexible rim elastically connects the one or more flexible seals to the outer hull;
         the rigid leg rigidly connects the flexible seals to the bracket;
         the bracket is mechanically connected to the proximal side of the weight sensor; and
         the outer hull is mechanically connected to the distal side of the weight sensor.

2. The uroflowmetry device according to claim 1,
   wherein the core unit further comprises:
      a communication module;
      a microprocessor; and,
      an energy source;
   wherein the receptacle comprises a urine analysis sensor for providing a chemical analysis of urine; and
   wherein the weight sensor is configured for detecting when micturition is over.

3. The uroflowmetry device according to claim 2, further comprising a waterproof housing, in which at least the one or more accelerometers, the urine detector, the weight sensor, the communication module, the energy source, and optionally a proximity sensor, are embedded.

4. The uroflowmetry device according to claim 1, further comprising a proximity sensor.

5. The uroflowmetry device according to claim 1, further comprising an inductive power module.

6. The uroflowmetry device according to claim 1, further comprising a memory module.

7. The uroflowmetry device according to claim 1, wherein the one or more accelerometers measures lateral acceleration and uses movement cancellation filters to cancel out particular movement artefacts.

* * * * *